United States Patent
Witt et al.

(10) Patent No.: US 10,166,031 B2
(45) Date of Patent: Jan. 1, 2019

(54) METHOD AND APPARATUS FOR PREPARING AN IMPLANTATION SITE

(71) Applicant: Biomet Manufacturing, LLC, Warsaw, IN (US)

(72) Inventors: Tyler D. Witt, Warsaw, IN (US); Aaron P. Smith, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 566 days.

(21) Appl. No.: 14/500,001

(22) Filed: Sep. 29, 2014

(65) Prior Publication Data

US 2015/0119892 A1    Apr. 30, 2015

Related U.S. Application Data

(63) Continuation-in-part of application No. 14/065,718, filed on Oct. 19, 2013.

(51) Int. Cl.
*A61B 17/32*        (2006.01)
*A61B 17/16*        (2006.01)

(52) U.S. Cl.
CPC ........ *A61B 17/1668* (2013.01); *A61B 17/164* (2013.01); *A61B 17/1659* (2013.01)

(58) Field of Classification Search
CPC .............. A61B 17/1688; A61B 17/164; A61B 17/1659; F16B 2001/0035; Y10T 403/7039
USPC ......................... 606/79–85; 403/361, DIG. 1
See application file for complete search history.

(56) References Cited

U.S. PATENT DOCUMENTS

| | | | |
|---|---|---|---|
| 4,281,420 A | 8/1981 | Raab et al. | |
| 4,336,618 A | 6/1982 | Raab et al. | |
| 4,491,987 A | 1/1985 | Park | |
| 4,795,472 A | 1/1989 | Crowninshield et al. | |
| 4,963,155 A | 10/1990 | Lazzeri et al. | |
| 5,013,324 A | 5/1991 | Zolman et al. | |
| 5,018,285 A | 5/1991 | Zolman et al. | |
| 5,089,003 A | 2/1992 | Fallin et al. | |
| 5,156,624 A | 10/1992 | Barnes | |
| 5,171,324 A | 12/1992 | Campana et al. | |
| 5,192,323 A | 3/1993 | Shetty et al. | |
| 5,326,362 A | 7/1994 | Shetty et al. | |
| 5,441,501 A | 8/1995 | Kenyon | |
| 5,480,453 A | 1/1996 | Burke | |
| 5,496,375 A | 3/1996 | Sisk et al. | |
| 5,569,255 A | 10/1996 | Burke | |
| 5,624,445 A | 4/1997 | Burke | |
| 5,702,485 A | 12/1997 | Burke et al. | |

(Continued)

OTHER PUBLICATIONS

Bio-Moore® Modular Prosthesis, Biomet Orthopedics, Inc., 12 pages (2001).

(Continued)

*Primary Examiner* — Zade Coley
*Assistant Examiner* — Jessica Weiss
(74) *Attorney, Agent, or Firm* — Schwegman Lundberg & Woessner, P.A.

(57) ABSTRACT

A bone preparation system, such as a broach, includes at least a first member and a second member. The first member and the second member may be connected. Both the first member and the second member, when attached to the first member, are configured to directly contact and broach an anatomy.

19 Claims, 11 Drawing Sheets

(56) References Cited

U.S. PATENT DOCUMENTS

| | | | | |
|---|---|---|---|---|
| 5,766,261 | A | * | 6/1998 | Neal ............ A61B 17/1659 606/85 |
| 6,126,694 | A | * | 10/2000 | Gray, Jr. ............ A61B 17/1659 623/22.11 |
| 7,189,024 | B2 | | 3/2007 | Cameron |
| 7,229,078 | B2 | * | 6/2007 | Lechot ............ A61B 17/1666 279/79 |
| 9,370,374 | B1 | * | 6/2016 | Ridde ............ A61B 17/1666 279/79 |
| 2004/0267266 | A1 | * | 12/2004 | Daniels ............ A61B 17/162 606/80 |
| 2012/0089146 | A1 | * | 4/2012 | Ferko ............ A61B 17/1617 606/87 |
| 2015/0119893 | A1 | | 4/2015 | Witt | |

OTHER PUBLICATIONS

Quick-Connects Brochure, Swagelok™ Company, www.swagelok.com, 20 pages (2013).
Restoration HA Hip System for Revision Surgery, Surgical Protocol, Osteonics Corp., 18 pages (1995).
VerSys® Advocate V-Lign® and Non V-Lign Cemented Prosthesis Surgical Technique, Zimmer, Inc., 97-7850-002-00 Rev1, 16 pages (Mar. 2009).
VerSys® Beaded FullCoat Revision Hip Surgical Technique, Zimmer, Inc., 32 pages (Apr. 2009).
VerSys® Epoch® Fullcoat Hip System Surgical Technique, Zimmer, Inc. (97-4088-102-00); 34 pages (Apr. 2010).
VerSys® Fiber Metal MidCoat and Beaded MidCoat Hip Prosthesis Surgical Technique, Zimmer, Inc., 97-7841-102-00, 18 pages (Aug. 2006).
VerSys® Fiber Metal Taper Hip Prosthesis Surgical Technique, Zimmer, Inc. (97-7862-102-00_Rev2),16 pages (Jan. 2011).
VerSys® Heritage® CDH Hip Prosthesis Surgical Technique for CDH Hip Arthroplasty, Zimmer, Inc., 97-7857-004-00, 14 pages (Nov. 2001).
VerSys® LD/Fx Cemented and Press-Fit Hip Prosthesis Surgical Technique, Zimmer, Inc. 97-7831-102-00, 12 pages (Apr. 2008).
Vision® Hip System, Biomet, Inc., 8 pages (1998).
Zimmer® VerSys® Trial Head Surgical Technique, Zimmer, Inc., 97-8018-001-00 Dec. 13, 2012, 6 pages (2012).
"U.S. Appl. No. 14/065,718, Final Office Action dated Jun. 16, 2016", 23 pgs.
"U.S. Appl. No. 14/065,718, Non Final Office Action dated Feb. 1, 2016", 21 pgs.
"U.S. Appl. No. 14/065,718, Non Final Office Action dated Dec. 16, 2016", 24 pgs.
"U.S. Appl. No. 14/065,718, Response filed Mar. 16, 2017 to Non Final Office Action dated Dec. 16, 2016", 12 pgs.
"U.S. Appl. No. 14/065,718, Response filed Jun. 1, 2016 to Non Final Office Action dated Feb. 1, 2016", 10 pgs.
"U.S. Appl. No. 14/065,718, Response filed Nov. 15, 2016 to Final Office Action dated Jun. 16, 2016", 10 pgs.
"U.S. Appl. No. 14/065,718, Final Office Action dated Jun. 8, 2017", 23 pgs.

* cited by examiner

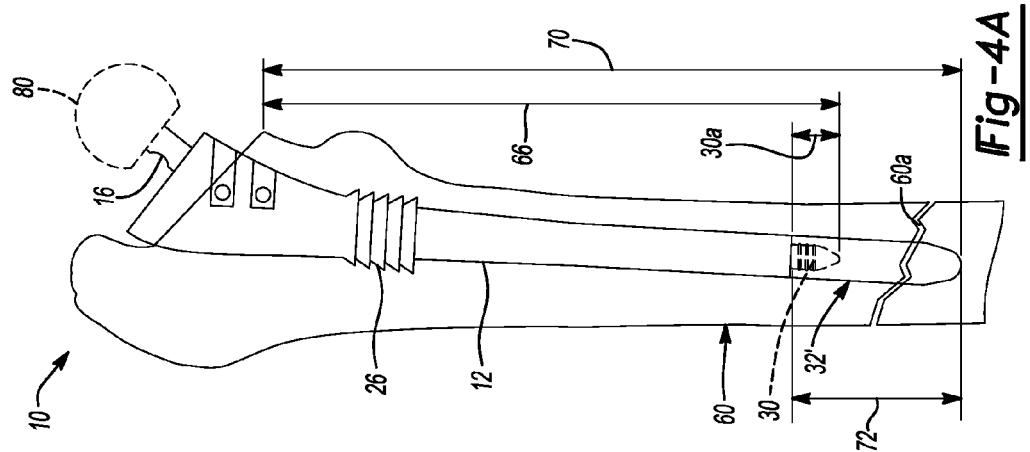
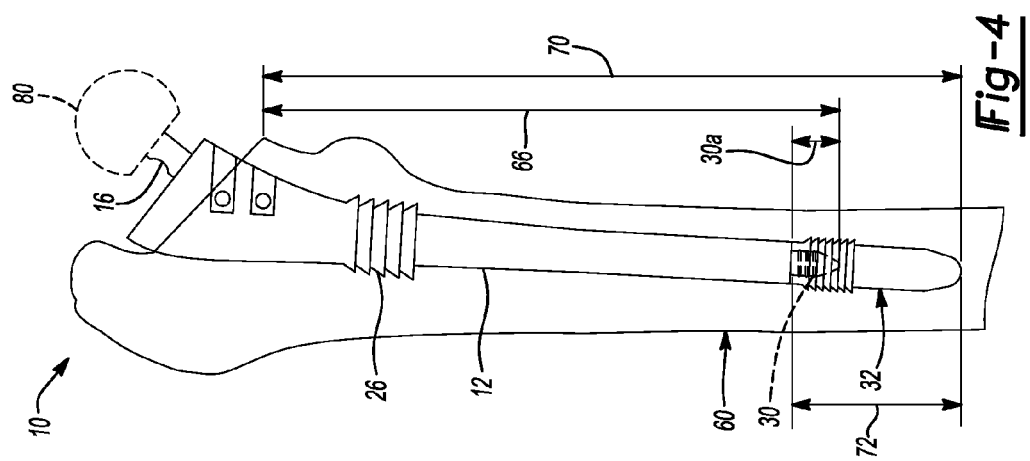
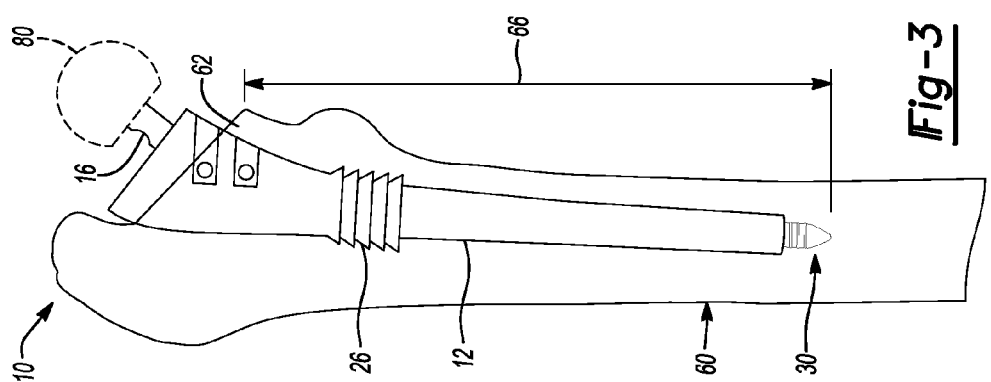

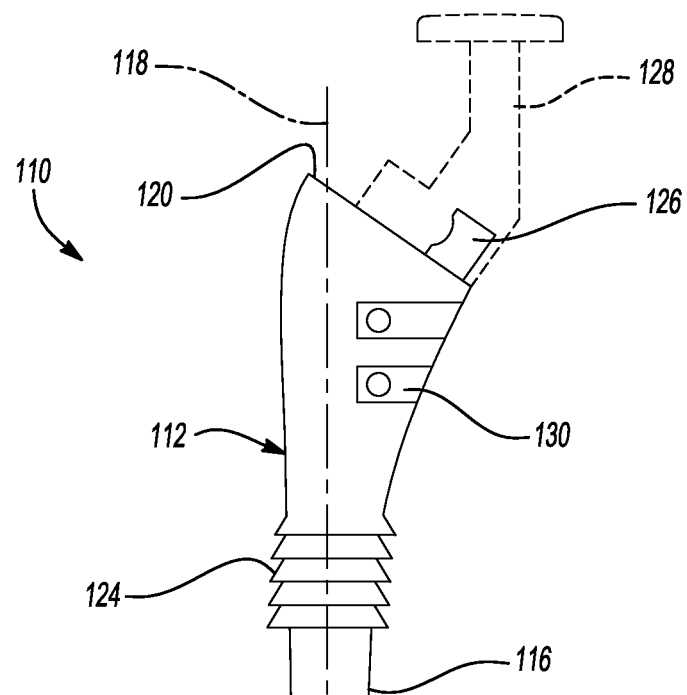
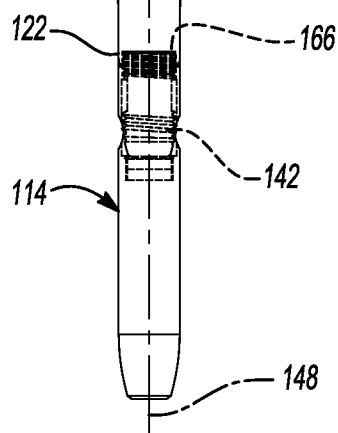
Fig-6B

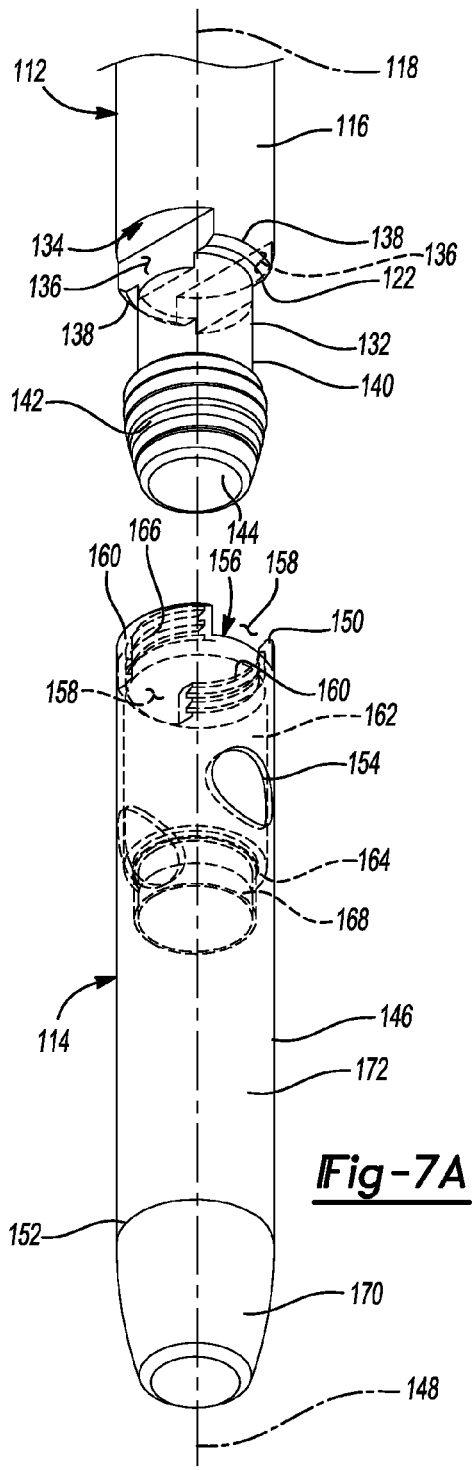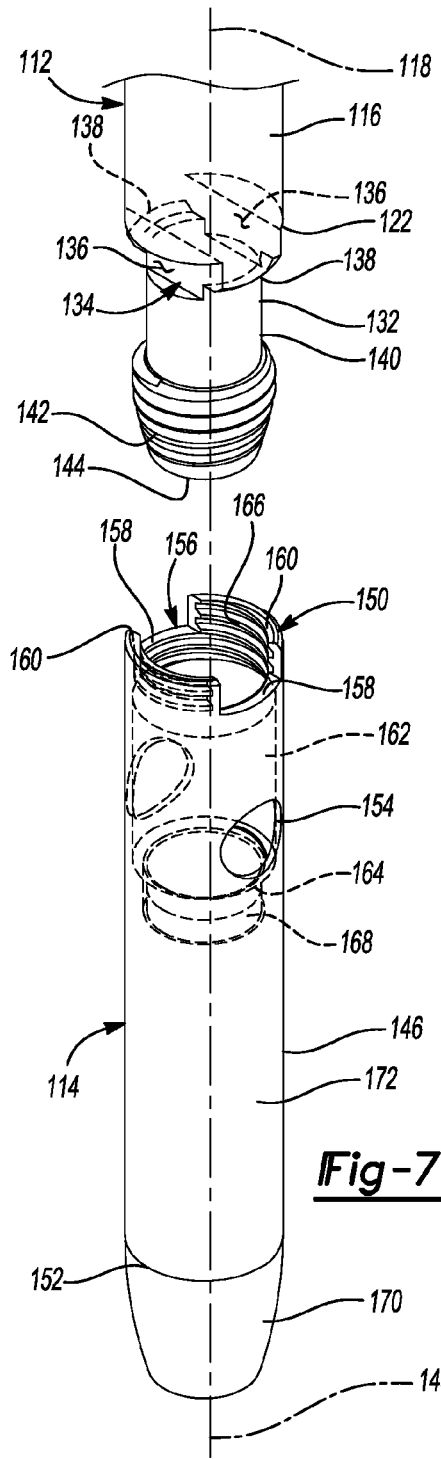

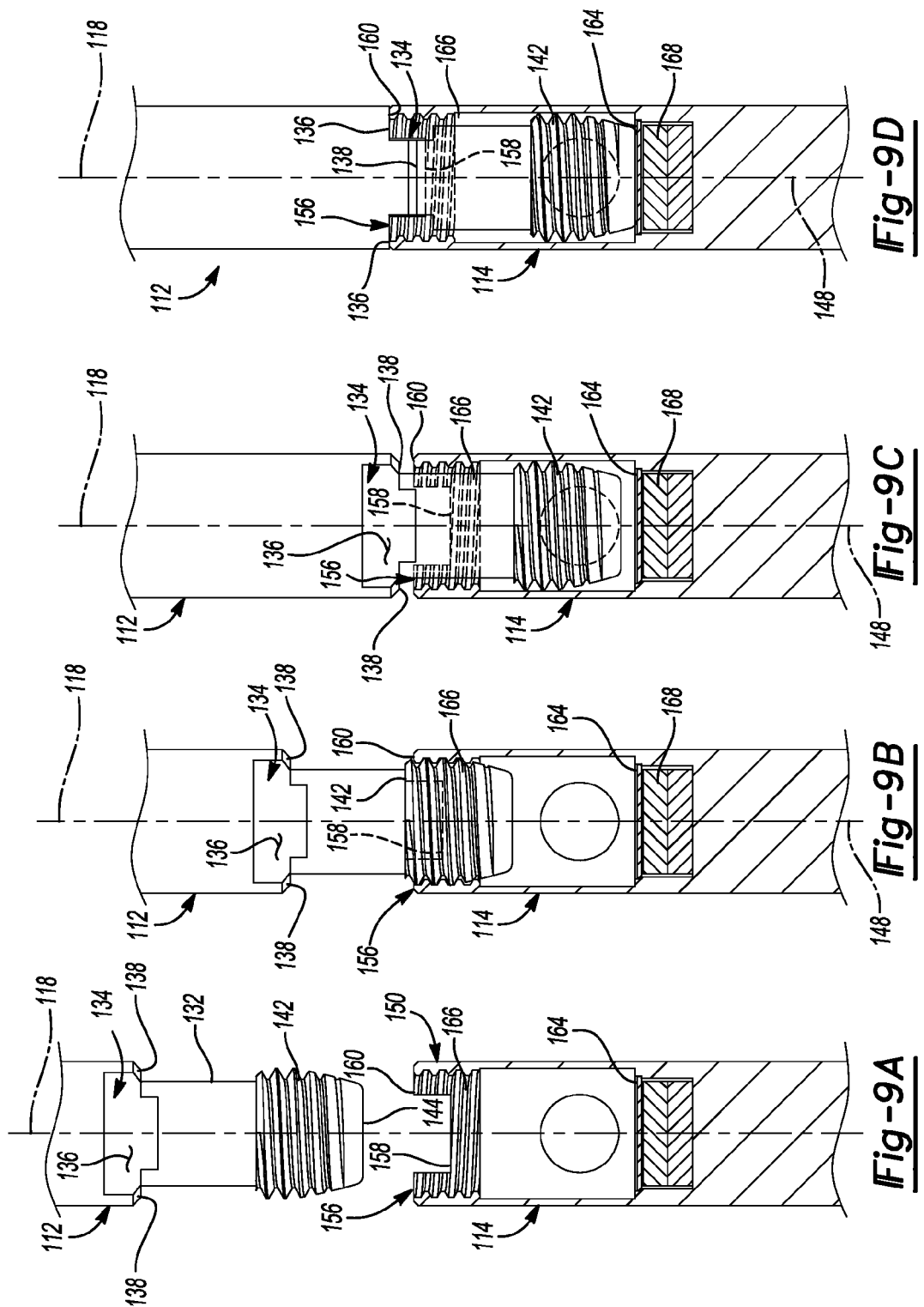

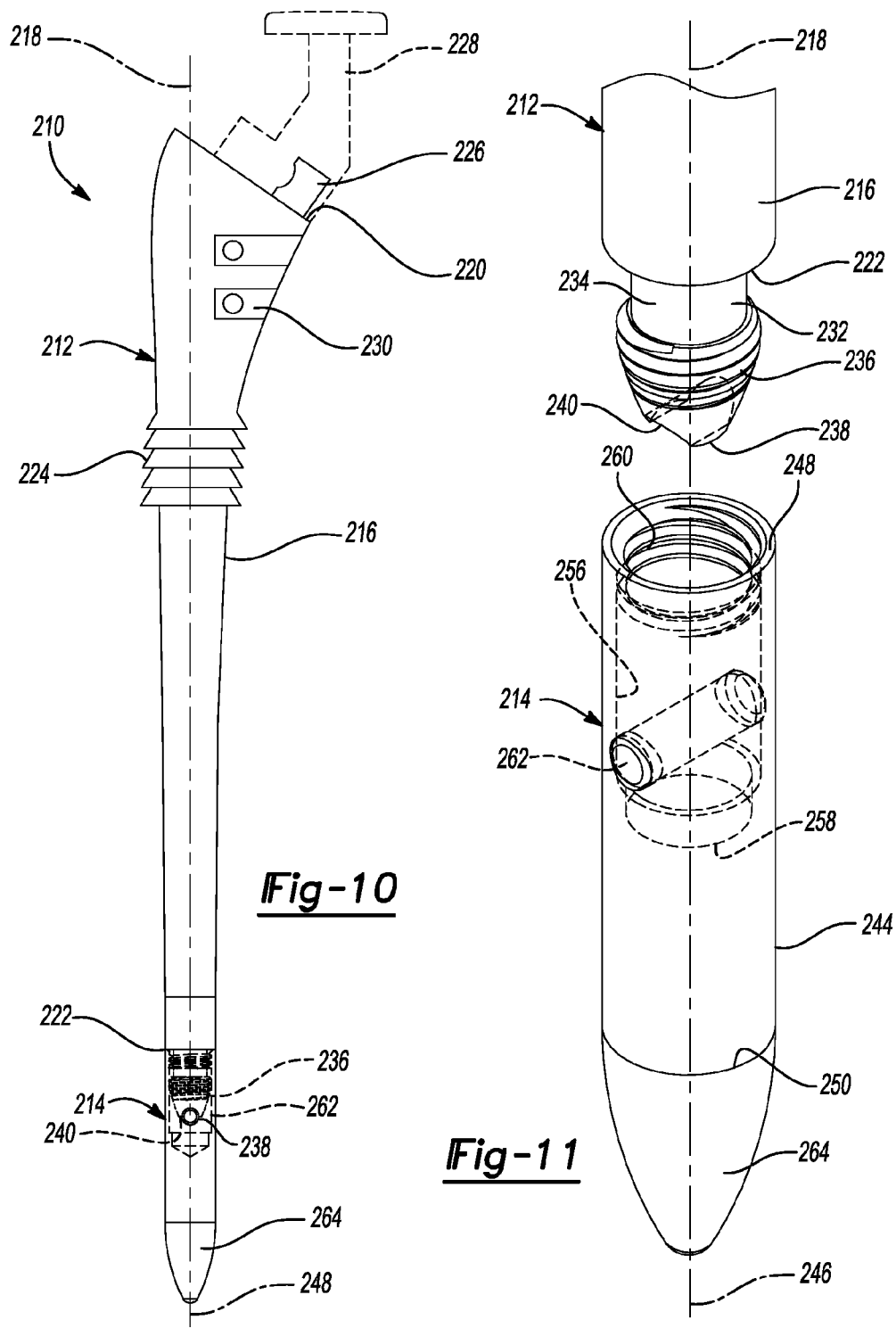

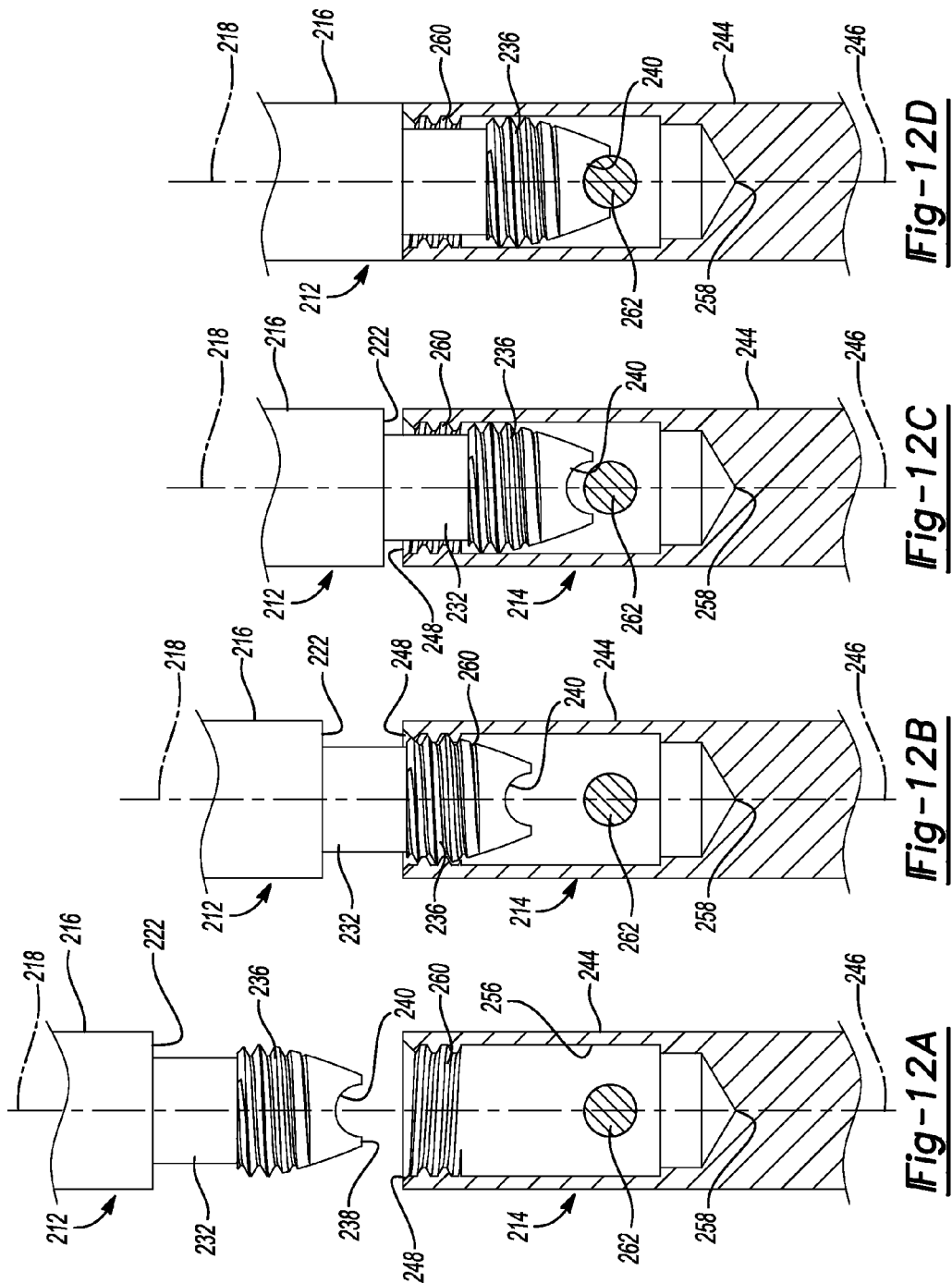

METHOD AND APPARATUS FOR PREPARING AN IMPLANTATION SITE

CROSS-REFERENCE TO RELATED APPLICATIONS

This application is a continuation-in-part of U.S. patent application Ser. No. 14/065,718 filed on Oct. 29, 2013. The entire disclosure of the above application is incorporated herein by reference.

FIELD

The subject disclosure relates to surgical instrumentation, and particularly to a broach for preparing a long bone for an implantation procedure and prosthesis.

BACKGROUND

This section provides background information related to the present disclosure which is not necessarily prior art.

A bone in an anatomy may be prepared for a procedure, such as implantation of a prosthesis. Bones can include long bones such as a femur, tibia, humerus, and other long bones of a human anatomy and equivalent long bones of other anatomies. In preparing long bones for implantation of the prosthesis portions of the bones can be removed, such as an intramedullary canal. For example, preparing the long bone for an implantation generally includes preparing a recess or opening to receive the implant member.

In preparing the long bone for an implant member, a reamer, broach, rasp or other instrument may be used to remove portions of the interior of the long bone. Generally, at least a portion of the intramedullary canal is removed using a selected instrument. When performing the long bone preparation, a selected length of removal of material is achieved using a plurality of lengths of rasp or broaches. A user selects the appropriate length rasp or broach to be used to remove the material from the interior of the bone.

SUMMARY

This section provides a general summary of the disclosure, and is not a comprehensive disclosure of its full scope or all of its features.

A bone preparation system, such as a broach, includes at least a first member and a second member. The first member and the second member may be connected. Both the first member and the second member, when attached to the first member, are configured to directly contact and broach an anatomy.

A modular system allows for user selection of a length of removal of an intramedullary canal. The system can include a first or main member that is able to rasp and/or broach a first length of a bone. The system further includes at least one or only one modular members that can be connected to the main member to allow for a second length rasp and/or broach or bone removal. The main member can be used without any additional modular pieces, particularly at a distal end, to directly broach and/or rasp the bone. Accordingly, the main member can be used to perform a broach and/or rasp without any additional distal attachments. It is understood that the main member can be connected to a handle to assist in guiding or moving the main member into the long bone for broaching the bone.

Further, the system can be used to prepare an interior of the bone. The preparation of the interior of the bone can be referred to by any appropriate term. It is understood, herein, that reference to either one of broach, ream, resect, rasp is not intended, unless specified otherwise, to disregard or not allow other types of bone preparation and removal. Thus, the system may be a rasp, a broach, etc.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is an environmental view of a main body of the broach system positioned in a long bone;

FIG. 4 is an environmental view of the broach system including the main body and attachment member in a long bone;

FIG. 4A is an environmental view of the broach system including the main body and an attachment member, according to various embodiments, in a long bone.

FIG. 6B is an assembled view of a broach system including a main body according to various embodiments and an extension member according to various embodiments, shown in partial phantom;

FIG. 7A is an exploded view of the main body and the extension member of the broach system FIG. 6A;

FIG. 7B is an exploded view of the main body and the extension member of the broach system FIG. 6A;

FIGS. 9A-9D is a method of coupling the main body and the extension member of the broach system of FIG. 6A;

FIG. 10 is an assembled view of a broach system including a main body according to various embodiments and an extension member according to various embodiments;

FIG. 11 is an exploded view of the main body and the extension member of the broach system of FIG. 10; and FIGS. 12A-12D is a method of coupling the main body and the extension member of the broach system of FIG. 10.

Corresponding reference numerals indicate corresponding parts throughout the several views of the drawings.

DETAILED DESCRIPTION

Example embodiments will now be described more fully with reference to the accompanying drawings.

Figure 1A:
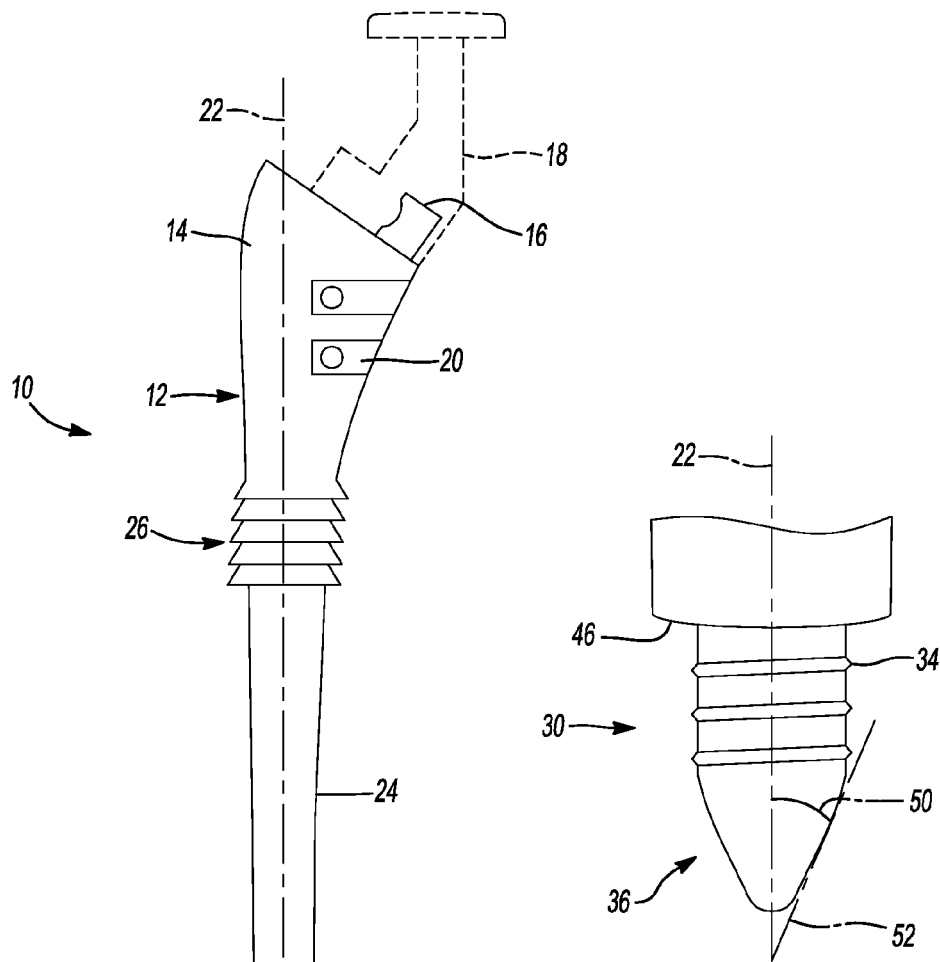
FIG. 1A is an exploded view of a broach system including a main body and an extension member.

A bone preparation system can include a broach assembly 10 illustrated in FIG. 1A. The broach assembly 10 can include various portions for preparing a bone for implantation of a prosthesis, such as broaching a long bone. In broaching a long bone, portions of an interior of the long bone, such as intramedullary canal, are removed. It is understood, however, that a similar instrument can include a rasp, a file, or other instrumentation that can be driven substantially axially into a long bone for removing or loosening portions of the interior of the long bone. Broaches generally can include selected single broaches such as the Taperloc® Hip System or Vision® Hip System sold by Biomet, Inc. having a place of business in Indiana, USA and the broach used with the Echo® Bi-Metric® Hip Stem or BIO-Moore® II Modular Prosthesis System, also sold by Biomet, Inc.

Returning reference to FIG. 1A, a first member can include a main body 12. The main body 12 can include an upper or proximal end or portion 14. A handle or neck connection portion 16 can extend or be formed with the proximal portion 14. The connection portion 16 can connect to a handle 18 (shown in phantom). The handle 18 can be driven with a hammer or other appropriate instrument (not specifically illustrated) to drive the broach assembly 10 into the selected anatomy, as discussed further herein. The connection portion 16 can also allow for connection of trial portions, such as a trial neck, a trial head (FIGS. 3 and 4) or other trial members to be trialed when positioned within the anatomy. Trialing using the broach assembly 10 can allow for determination of an appropriate head size, neck length, or other selected features of a final prosthetic system. The final or implanted prosthetic system can include a proximal femur implant, a distal femur implant, a humerus implant, or other appropriate prosthesis. The main body 12 can further include one or more slots 20 that can be interconnected with tables or platforms that can contact the anatomy to limit the movement of the broach assembly 10 into the anatomy.

The main body 12 can extend along a longitudinal axis 22 that extends through the proximal portion 14 and along a shaft portion 24. Formed along a selected portion of the body 12, including an entire length or substantially over at least to the length that the shaft 24, can be a cutting surface. The cutting surface can be one or a plurality of cutting edges or cutting ledges 26. The cutting ledges 26 can scrape along or engage the bone on the interior of the long bone to remove portions of the interior of the long bone. Although illustrated in FIG. 1A is only a short series of the cutting edges 26, it is understood that the cutting edges can extend along substantially the entire length of the main broach body 12, or at least a portion thereof. It is also understood that the cutting edges 26 can be sharpened and extend any selected length from the central longitudinal axis 22 depending upon the amount of bone or aggressiveness of broaching selected or required within the bone.

Near a distal end of the main body 12 is a connection region or portion 30, discussed in further detail herein, operable to allow for a connection of a modular extension member 32. The connection portion 30 can be formed as one piece with the main body 12, such as by machining from bar stock, forging, or casting. Alternatively, the connection portion 30 can be connected to the main body 12, such as by welding, brazing or selected adhesive.

The connection portion 30 can include a connecting section, such as a threaded region 34. The threaded region 34 can have external threads that can engage internal threads in the extension member 32. It is understood, however, that the connecting region of the connection portion can include alternative and/or additional connection features such as taper fits, snap fits, etc. The connection portion 30 can also include a distal tip 36. The distal tip 36 can be formed and/or configured to directly engage the bone, as discussed further herein.

Figure 2:
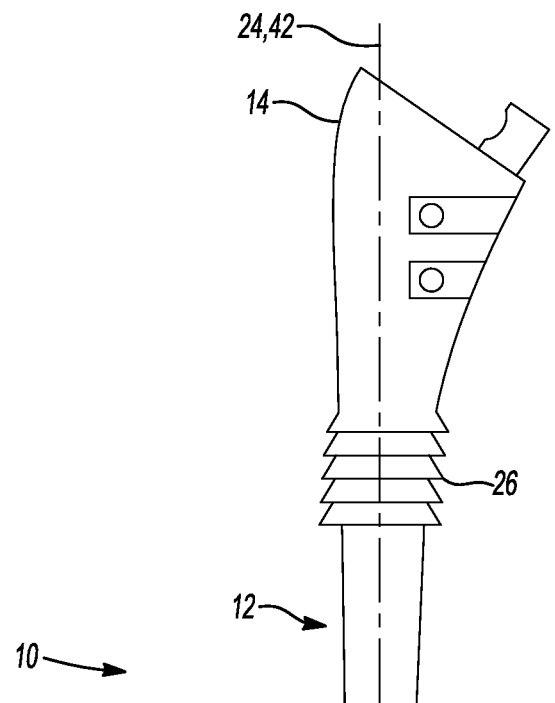
FIG. 2 is an assembled view of the broach system.

The extension member 32 can then be threaded onto the connection portion 30 to engage the main body 12, as illustrated in FIG. 2. The extension member 32 can also include one or more cutting edges 40. The cutting edges 40 can include a feature similar to the cutting edges 26, discussed above, including a length extending from a central longitudinal axis 42 of the extension member 32 or other selected feature to engage the anatomy for removing selected bone. The extension member 32 can also include a distal end 44 that can taper towards the central longitudinal axis 42. When connected, the cutting edges 40 of the extension can form a single continuous cutting surface with the cutting edges 26 of the main body 12.

Figure 1B:
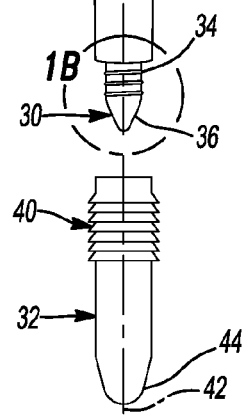
FIG. 1B is a detailed view of a distal end of the main body of the broach system.

Illustrated in FIG. 1B is the connection region 30. As discussed above, the connection portion 30 can include threads 34 in the connection region to engage internal threads of the extension member 32. A ledge or shoulder 46 defines an extent of the connection region, and generally is at a proximal end of the connection region 30. The ledge 46 can engage the extension member 32 to limit travel of the extension member 32.

The tapered tip 36 can also have a curved outer surface or a substantially flat or straight outer surface. The outer surface of the tip 36, however, can define a taper angle 50 between the central axis 22 and a line 52 that is either tangent to the exterior of the tapered tip 36 or is defined as a line extending along the flat tapered surface 36. As discussed further herein, this allows the tapered distal end 36 of the connection region 30 to be positioned within a portion of the long bone in an appropriate manner to allow for broaching of the long bone with the main body 12 alone without connection of any other members, including the extension member 32.

With continuing reference to FIGS. 1A and 1B, and further reference to FIG. 2, the assembly 10 can be assembled, as specifically illustrated in FIG. 2, for use as a combined system. As illustrated in FIG. 2 the extension member 32 can be connected to the main body 12 to form a substantially continuous broach assembly extending from the proximal portion 14 to the distal tip 44 of the extension member 32. The assembly 10 can extend along the assembled longitudinal axis 22, 42 such that the assembly 10, in the assembled state, will broach a single area that is substantially continuous along a combined length of the body 12 and the extension member 32. Further, the transition between the main body 12 and the extension member 32 is substantially congruent and smooth. Accordingly, the exterior of the extension member 32 at the boundary with the main body 12, allows the extension member 32 to engage the shoulder 46 of the main body 12 such that the main body 12 and the extension member 32 form a single unit. It is understood, however, that the connection or the boundary between the extension member 32 and the main body 12 can also be non-congruent such that it can form a cutting edge or different size rasp region. Regardless, the assembly can be formed to broach a bone along the combined and generally aligned axes 22, 42.

Further, by the connection of the extension member 32 with the main body 12, the cutting edges 40 of the extension member 32 can form a cutting surface or exterior cutting boundary with the cutting edge 26 of the main body 12. Again, it is understood, that the outer or external cutting surface can be substantially parallel, cylindrical, or may be tapered such that the cutting diameter at the distal end 42 of the extension member 32 is less than the cutting diameter near the proximal end 14 of the main body 12. Further, it is understood that the extension member 32 can be connected to the main body 12 in any appropriate manner including by the interaction with the threads 34, as discussed above or with other appropriate connection mechanisms. For example, a snap connection or a taper fit connection.

With reference to FIGS. 3 and 4 the broach assembly 10 is illustrated during use. With specific reference to FIG. 3, the main body 12 can be used alone to broach a long bone, such as a femur 60. The femur 60 can be prepared in an appropriate manner, such as resection of a femoral head and neck to provide a resected surface 62. The main body 12 can then be inserted into the femur 60, such as into an IM portion of the femur 60, using appropriate mechanisms, as discussed above. For example, the handle 18 can be connected to the connection portion 16 and the main body 12 can be driven into the femur 60. The main body 12 alone can broach a portion of the femur 60 due to the interaction of the cutting edges 26 with the interior of the femur 60 and the shape and configuration of the attachment portion 30 at the distal end of the main body 12. As discussed above, the terminal end of the attachment portion 30 can include a taper, curve, or other appropriate configuration to allow the main body 12 alone to be inserted and broach the femur 60.

Alone, the main body 12 can be used to broach a selected length or distance 66 into the bone of the femur 60, as illustrated in FIG. 3. The distance 66 can be any appropriate length, such as a main body length 66 that is a length of the main body 12. The main body length 66 can be less than a combined length or distance 70, as illustrated in FIG. 4. Accordingly, based upon a pre-planning, surgeon selection, or other requirement for a procedure, the main body 12 can be used to broach the femur 60 to the first length 66. The first length 66 may be selected based upon the size of the implant to be implanted into the femur 60, the size of the patient being broached, or other appropriate considerations. Additionally, the main body 12 can receive a trial head 80 (shown in phantom) for trialing after placement of the main body 12 within the femur 60. It is understood that other trial portions can also be connected with the connection portion 16 according to various trialing techniques.

With specific reference to FIG. 4, the second or attached distance 70 can include a distance that is greater than the first distance 66 and can be defined as a broach distance or length based upon the length of the main body 12 and the extension member 32, which can be connected to the main body 12, as illustrated in FIG. 4. The second distance 70 can include a combination of the first distance 66 and an attachment or extension distance 72 minus a distance 30a of the attachment portion 30. The attachment distance 72 can be dependent upon the length of the extension member 32 and can also be selected for various procedures, such as a length of the patient's femur 60, an implant to be positioned within the femur 60, or other considerations. Nevertheless, the connection of the extension member 32 to the main body 12 can be used to form the assembly 10 that can broach the second length 70 into the femur 60. Additionally, a trial head 80 or other trial portion can be interconnected with the connection portion 16.

With additional reference to FIG. 4A, according to various embodiments, a smooth extension 32' can be connected with the main body 12. The extension 32' can be made with the attachment portion 30 in any appropriate manner, including those discussed above. The smooth extension 32' can have an exterior surface that is substantially smooth and does not include any of the cutting edges 40 as illustrated and included in the extension 32. Accordingly, the smooth extension 32' may be included to not broach or cut any bone, such as the femur 60, but can be positioned within the bone 60 to assist in stabilization of the main body 12 of the broach assembly. Accordingly, the smooth extension 32' can be connected with the main body 12 to provide for a selected length of a combination of main body 12 and the extension 32' without broaching a distal portion or extension into the femur 60. According to various embodiments, as is generally understood by one skilled in the art, a reamer or other instrument can ream a portion of the bone 60. For example, the bone 60 may have a fracture or weakened portion 60a and the extension 32' can extend beyond the weakened or fractured portion 60a, as illustrated in FIG. 4A. Accordingly, the smooth extension 32' can engage a portion of the bone 60, such as a portion beyond the fracture 60a, for stabilizing the assembled broach assembly during a procedure. It may be selected by a user to provide the smooth extension 32' to engage a portion of the bone 60 beyond the fracture portion 60a for stabilizing the assembled broach assembly and/or selecting a final length of an implant, such as a femoral stem.

As discussed above, the main body 12 can be used alone to broach an appropriate bone, such as the femur 60. The connection portion 30 of the main body 12 can interact with the femur 60 alone without any member placed thereon. Accordingly, the main body 12 can be used alone to broach a selected distance, such as the first distance 66 into the bone 60. Only a single member, such as the extension member 32, need be interconnected with the main body 12 to broach the second distance 70. It is understood that the assembly 10 may include other connections, such as an intermediate connection between the extension member 32 and the main body 12 or have a plurality of extension members 32 of the varying lengths.

Figure 5:
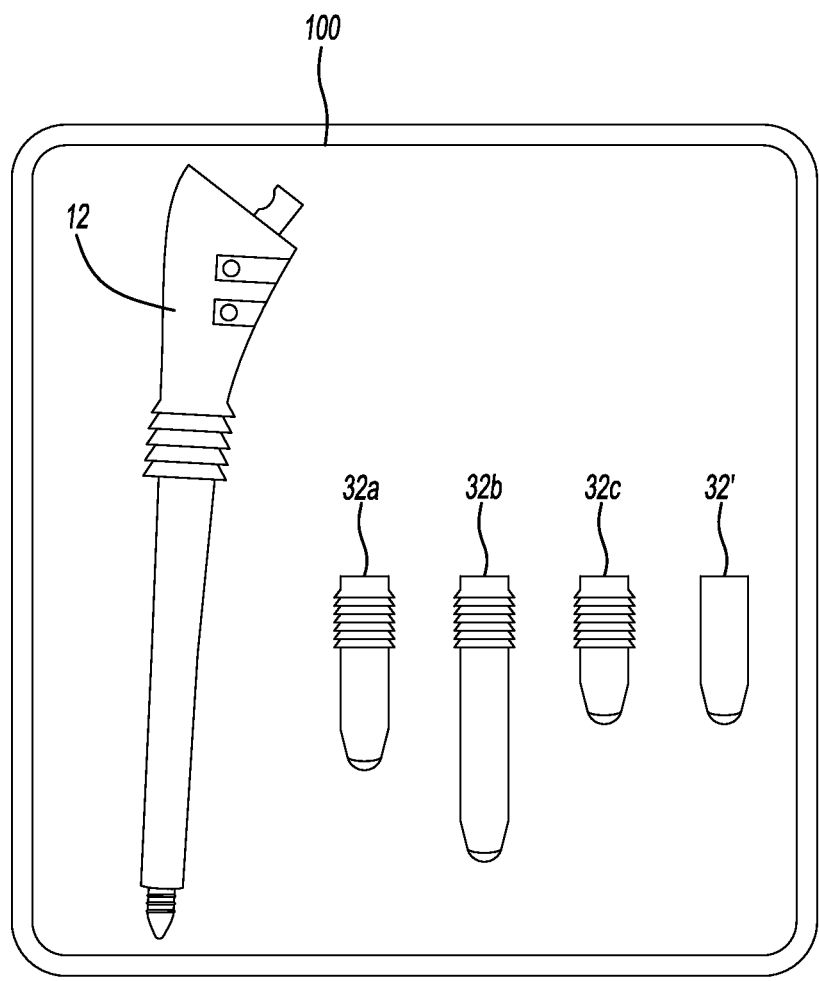
FIG. 5 is a kit view of a broach system including a main body and a plurality of extension members.

For example, as illustrated in FIG. 5, a kit or system 100 can include the main body 12 and a plurality of the extension member 32, including extension members 32a, 32b, and 32c. Each of the extension members 32 can include different lengths such that the attachment length 72 may be varied depending upon the selected extension members 32 connected to the main body 12. For example, the extension member 32a can have a first distance that is less than a second length of the second extension member 32b while the first distance of the first extension member 32a can be greater than a third length of the third extension member 32c. Thus, based upon the selection of the extension members 32a, 32b, and 32c, the second length 70 can be varied. Also, according to various embodiments, one or more of the smooth extensions 32' can be included within the kit 100. Thus, the single kit 100 can include broach extensions for cutting and/or for stabilizing and not cutting the bone 60. A user can select the length for broaching and/or trialing. It is also understood that the extension members 32 can be connected to the main body 12 after the beginning of a procedure based upon a user selection, such as confirming a length broached within the femur 60.

Figure 6A:
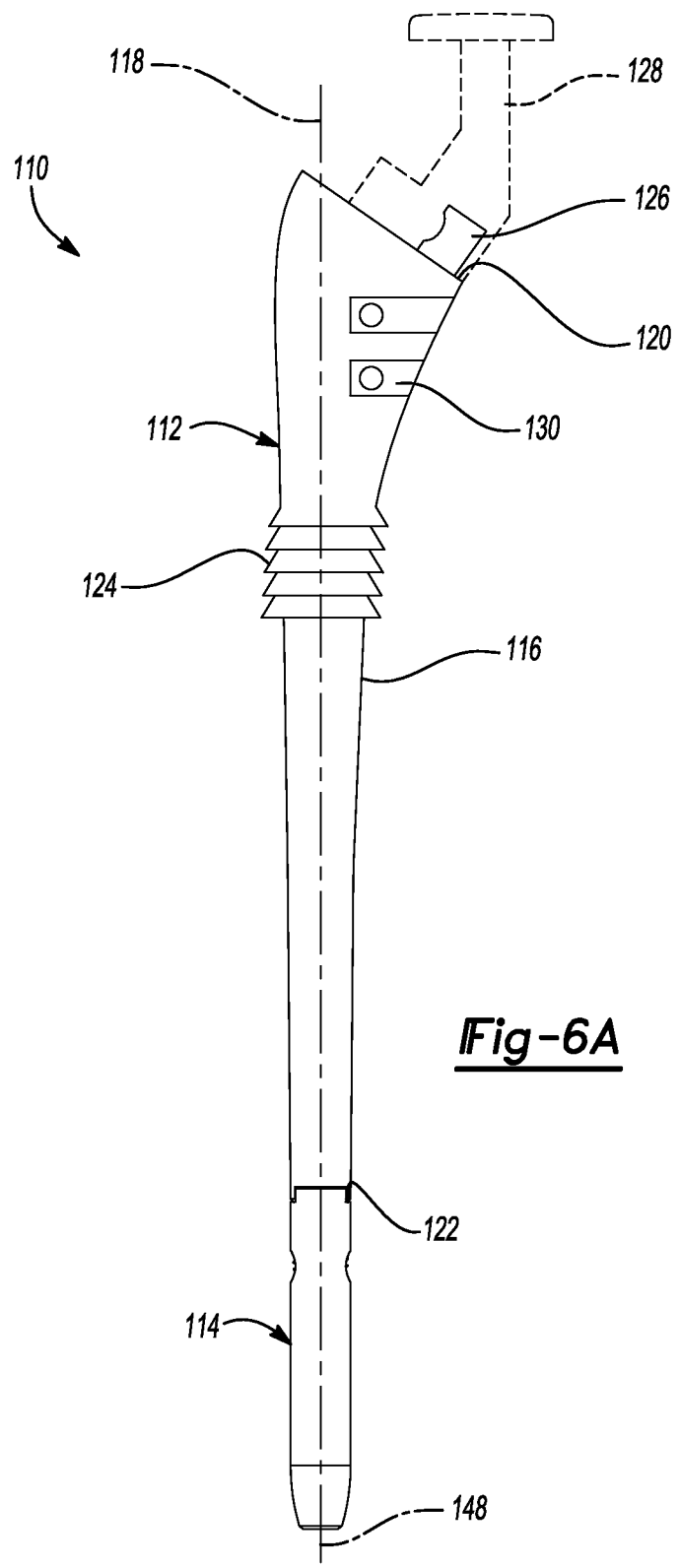
FIG. 6A is an assembled view of a broach system including a main body according to various embodiments and an extension member according to various embodiments.

With reference to FIGS. 6A and 6B, and according to various embodiments, a bone preparation system including a broach assembly 110 is shown. The broach assembly 110 can include a main body 112 and an extension member 114. As will be described further below, in one exemplary and non-limiting use, the main body 112 can be selectively coupled with the extension member 114. Further, it is understood, that the kit 100, illustrated in FIG. 5, can include any of the disclosed broach portions and configurations disclosed herein.

The main body 112 can be substantially similar to the main body 12 described above. For example, the main body 112 can include an elongated shaft 116 extending along a first longitudinal axis 118 between a proximal end 120 and a distal end 122. One or more cutting surfaces or cutting ledges 124 can be formed along an entire length of the elongated shaft 116 or along a selected portion thereof. The cutting ledges 124 can extend laterally outward from the elongated shaft 116 any appropriate selected distance. The distance may depend on the amount of bone or the aggressiveness of broaching required within the bone, for example.

At the proximal end 120, the main body 112 can include a first connection portion 126, which may be a handle or neck connection portion. The first connection portion 126 can be configured to connect a handle 128 (shown in phantom) to impact the broach assembly 110 into a bone, for example. Alternatively, as shown in broach assembly 110' of FIG. 8, a trial portion 128' (shown as a femoral head in phantom) can be connected to a similar first connection portion 126' for trialing, for example. Referring back to FIG. 6A, the main body 112 can also include one or more slots 130 that are configured to be connected with tables or platforms to contact the bone during use and limit movement of the broach assembly 110 relative to the bone.

With additional reference to FIGS. 7A and 7B, the distal end 122 of the elongated shaft 116 of the main body 112 may include a second connection portion 132. The second connection portion 132 can selectively couple the main body 112 and the extension member 114. The second connection portion 132 can be formed as a unitary member with the main body 112 or can be formed as a separate member and permanently or removeably attached to the main body 112 by welding, brazing, fastening, or using other joining techniques. A first alignment feature 134, including a pair of first alignment notches 136 and a pair of first alignment projections 138, can be located at an upper end of the second connection portion 132 (i.e., at the distal end 122 of the elongated shaft 116 of the main body 112). A substantially smooth portion 140 can extend between the first alignment feature 134 and a first threaded portion 142. A distal end 144 of the second connection portion 132 may be formed in an appropriate configuration, such as the distal end 144 may be substantially flat, straight, or can include a taper. Further, the distal end 144 can be fabricated from a material having magnetic properties, or alternatively or additionally, the second connection portion 132 and/or the main body 112 as a whole can be fabricated from a material having magnetic properties. Further, the distal end 144 may be fabricated to include a material or portion that has magnetic properties. Similarly, a portion of material with magnetic properties may be connected to the distal end 144, such as by an adhesive, welding, etc.

With continued reference to FIGS. 6, 7A and 7B, the extension member 114 can include an elongated shaft 146 extending along a second longitudinal axis 148 between a proximal end 150 and a distal end 152. An opening 154 can extend through the elongated shaft 146 at a direction generally perpendicular to the second longitudinal axis 148. The opening 154 may be provided for various purposes, such as for cleaning the extension member 114 and allowing access to the interior of the extension member 114 for cleaning solution.

A second alignment feature 156, including a pair of second alignment notches 158 and a pair of second alignment projections 160, can be located at the proximal end 150 of the extension member 114. The second alignment feature 156 can be configured to matingly engage the first alignment feature 134 of the main body 112. A bore 162 can extend from the proximal end 150 of the extension member 114 to a bore distal end 164. The bore 162 can include therein a second threaded portion 166 and a magnet or magnetic portion 168. The second threaded portion 166 can be configured to threadably engage the first threaded portion 142 of the main body 112, and the magnetic portion 168 can be configured to magnetically engage at least the distal end 122 of the main body 112. A distal tip 170, extending from the distal end 152 of the elongated shaft 146, can taper towards the second longitudinal axis 148. The distal tip 170 can be configured to engage a bone of the anatomy when the extension member 114 is selectively coupled with the main body 112. According to various embodiments, the elongated shaft 146 may engage an interior of a femur.

An outer surface 172 of the elongated shaft 146 can be substantially smooth. In one configuration, similar to one of the configurations recited in the description of the broach assembly 10 above, when the extension member 114 is selectively coupled with the main body 112, the substantially smooth outer surface 172 can be positioned within a bone to assist in stabilizing the broach assembly 110. The outer surface 172 of the elongated shaft 146 can also, or alternatively, include cutting surfaces or ledges (not shown) that can be similar to the cutting ledges 40 included on the extension member 32 described above. Accordingly, in another configuration, similar to another one of the configurations recited in the description of the broach assembly 10 above, when the extension member 114 is selectively coupled with the main body 112, the cutting ledges can broach a bone.

Moreover, while the elongated shaft 146 of extension member 114 can be generally straight as shown in FIGS. 6, 7A and 7B, the elongated shaft 146 can also include bends and/or other geometry. Selected geometries may be selected as generally corresponding to an anatomical shape of bones, like the elongated shaft 146' of extension member 114' selectively coupled to main body 112' shown in FIG. 8. Because the features and function of the extension member 114 and the extension member 114' are substantially common, a separate description of the extension member 114' is not provided herein.

Additionally, the extension member 114 can also include various lengths. A kit (not shown), similar to the kit 100 described above, can include multiple extension members having differing geometries and lengths. This can allow the broach assembly 110 to be customized and adapted for multiple uses and various applications, such as an intraoperative length and/or geometry selection.

According to one exemplary and non-limiting use that can be similar to one of the exemplary uses recited in the description of the broach assembly 10 described above, the second connection portion 132 of the main body 112 can be positioned within a portion of a bone to be broached. In other words, the main body 112 of the broach assembly 110 can be used without coupling any other member to the second connection portion 132, such as the extension member 114.

In another exemplary and non-limiting use that can be similar to another one of the exemplary uses recited in the description of the broach assembly 10 above, the main body 112 can be selectively coupled with the extension member 114. For example, based on pre-planning, surgeon selection, or other requirements, the main body 112 and the extension member 114 may be selected to be coupled to the main body 112. The coupling selection may be to extend length of the broach assembly 110, to provide the broach assembly 110 with a particular geometry to accommodate a particular size of a bone to be broached, or to accommodate an implant length to be implanted into a bone.

With reference to FIGS. 9A-9D, a method for selectively coupling the main body 112 with the extension member 114 will be described. As shown in FIG. 9A, the distal end 144 of the second connection portion 132 of the main body 112 can be positioned near the proximal end 150 of the extension member 114 such that the first and second longitudinal axes 118, 148 are generally collinear. The main body 112 and the extension member 114 can each be rotated in opposite directions about the first and second longitudinal axes 118, 148 until the first and second threaded portions 142, 166 threadably engage, as shown in FIG. 9B. Alternatively, one of the main body 112 and the extension member 114 can be rotated about a corresponding first and second longitudinal axis 118, 148 in a first direction, while the other of the main body 112 and the extension member 114 is not rotated, until the first and second threaded portions 142, 166 threadably engage.

Once the first threaded portion 142 threadably engages past the second threaded portion 166 (i.e., once the entire first threaded portion 142 is positioned between the second threaded portion 166 and the bore distal end 164) as shown in FIG. 9C, the main body 112 can rotate freely about the first longitudinal axis 118, and the extension member 114 can rotate freely about the second longitudinal axis 148 without the main body 112 and the extension member 114 threadably disengaging. Moreover, in this position, at least a portion of the second connection portion 132 of the main body 112 can move along the second longitudinal axis 148 of the extension member 114 between the second threaded portion 166 and the bore distal end 164. By matingly engaging the first and the second alignment features 134, 156 as shown in FIG. 9D, the main body 112 and the extension member 114 can be restricted from rotating freely. More specifically, once each of the second alignment notches 158 of the extension member 114 matingly engages a corresponding first alignment projection 138 of the main body 112, and each of the second alignment projections 160 of the extension member 114 matingly engages a corresponding first alignment notch 136 of the main body 112, the main body 112 and the extension member 114 can be restricted from rotating freely about each of the respective first and second longitudinal axes 118, 148. When the projections 138, 160 mate with the indents 136, 158, as illustrated, the projections 138, 160 are at least partially received in the indents 136, 158. It is not required, however, that the projections be bottomed out or completely contact (e.g. on all surfaces) the respective indents.

To a selected extent, the main body 112 and the extension member 114 may move axially relative to one another. However, magnetic engagement between the distal end 144 of the main body 112 and the magnetic portion 168 of the extension member 114 can restrict the main body 112 and the extension member 114 from moving along each respective longitudinal axis 118, 148 once the first and second alignment features 134, 156 are matingly engaged. Generally, the magnetic engagement operates to ensure that the extension member 114 maintains engagement with the main body 112 during insertion and removal of the broach assembly 110 from a bone.

Disassembly of the main body 112 and the extension member 114 can be accomplished by generally following the above coupling method in reverse. That is, the main body 112 and the extension member 114 can each be pulled in opposite directions along the first and second longitudinal axes 118, 148 with a force greater than the force of the magnetic engagement between the main body 112 and the extension member 114. Once magnetically disengaged, and once the first and second alignment features 134, 156 are matingly disengaged, the main body 112 and the extension member 114 can be rotated in opposite directions about the first and second longitudinal axes 118, 148 until the first and second threaded portions 142, 164 threadably disengage. Alternatively, one of the main body 112 and the extension member 114 can be rotated about the corresponding first and second longitudinal axes 118, 148 in a second direction that is different than the first direction, while the other of the main body 112 and the extension member 114 is not rotated, until the first and second threaded portions 142, 166 threadably disengage.

With reference to FIG. 10, and according to various embodiments, another system including a broach assembly 210 is shown. The broach assembly 210 can include a main body 212 and an extension member 214. As will be described further below, in one exemplary and non-limiting use, the main body 212 can be selectively coupled with the extension member 214. As discussed above, the broach assembly 210 may be used for preparing a bone for an implant and/or trialing during an implantation procedure.

The main body 212 can be substantially similar to the main body 12 and 112, described above. For example, the main body 212 can include an elongated shaft 216 extending along a first longitudinal axis 218 between a proximal end 220 and an opposing distal end 222. Also, one or more cutting surfaces or ledges 224 can be formed along an entire length of the elongated shaft 216, or along a selected portion thereof, and can extend any selected appropriate distance laterally outward therefrom.

Near the proximal end 220, the main body 212 can include a first connecting portion 226. The first connection portion 226 may be a handle or a neck connection portion for connecting a handle 228 (shown in phantom) for impacting the broach assembly 210 into the bone, or connecting a trial neck or a trial head (similar to that illustrated in FIG. 8) for trialing. The main body 212 can also include one or more slots 230 for interconnecting with tables or platforms to contact a bone and limit movement of the broach assembly 210 relative to the bone. It is understood that the broach assembly 210 may be used to broach any selected member, such as a wood or metal member or tube.

With additional reference to FIGS. 11 and 12A, the distal end 222 of the main body 212 can include a second connection portion 232. The second connection portion 232 may be formed as a unitary member with the main body 212 or formed as a separate member and permanently or removeably attached to the main body 212. The second connection portion 232 can include a generally smooth portion 234 extending from the distal end 222 of the main body 212 and a first threaded portion 236 located near at a distal end 238 of the smooth portion 234. The distal end 238 may be generally flat or straight and can include a first alignment feature or slot 240 having a generally semi-circular shape, for example.

The extension member 214 can include an elongated shaft 244 extending along a second longitudinal axis 246 between a proximal end 248 and a distal end 250. An opening (not shown), similar to the opening 154 of the extension member 114 described above, can extend through the elongated shaft 244 at a direction generally perpendicular to the second longitudinal axis 246. A bore 256 can extend from the proximal end 248 of the extension member 214 to a bore distal end 258. A second threaded portion 260 may be formed in a surface at least partially defining the bore 256. A second alignment feature or pin 262 having a generally cylindrical shape may also be placed or formed within the bore 256. The second threaded portion 260 can be configured to threadably engage the first threaded portion 236 of the main body 212. The pin 262 can be disposed intermediate the second threaded portion 260 and the bore distal end 258 at a direction generally perpendicular to the second longitudinal axis 246. A distal tip 264, extending from the distal end 250 of the elongated shaft 244, can taper towards the second longitudinal axis 246 and can be configured to engage a bone when the extension member 214 is selectively coupled with the main body 212.

The size of the pin 262 can be generally the same size as the slot 240 of the second connection portion 232 described above, or slightly smaller. The pin 262 can be configured to matingly engage or snap fit onto the slot 240 of the second connection portion 232. The pin 262 when engaged into the slot 240 may selectively hold the extension member 214 axially relative to the main body 212.

The elongated shaft 244 of the extension member 214 can be generally smooth or include cutting ledges, as discussed above. The elongated shaft 244 can also be provided in various geometries, such as straight or curved. Also, the elongated shaft 244 may be provided in varying lengths. Thus, a selected one or more of a plurality of the elongated shafts 244 may be coupled to the main body 212 for providing the broach assembly 210 to be customized and adapted for multiple uses and various applications.

According to one exemplary and non-limiting use that can be similar to one of the exemplary uses of the broach assembly 10, and 110 described above, the second connection portion 232 of the main body 212 can be positioned within a portion of a bone to be broached. In other words, the main body 212 of the broach assembly 210 can be used without coupling any other member to the second connection portion 232, such as the extension member 214 for example.

In another exemplary and non-limiting use that can also be similar to one of the exemplary uses of the broach assembly 10, and 110 described above, main body 212 can be selectively coupled with the extension member 214 to extend the length of the main body 212 in the broach assembly 210. For example, the length and/or the geometry of the broach assembly 210 may be selected to be modified to accommodate a particular size of a bone to be broached or to accommodate varying implant lengths to be implanted into the bone. Also, it is understood, that the broach assembly 210 may be selected to broach other appropriate selected members such as metal piping or wood portions.

With reference to FIGS. 12A-12D, a method for selectively coupling the main body 212 and the extension member 214 will be described. As shown in FIG. 12A, the distal end 222 of the elongated shaft 216 of the main body 212 can be positioned near the proximal end 248 of the extension member 214 such that the first and second longitudinal axes 218, 246 are generally collinear. With reference to FIG. 12B, each of the main body 212 and the extension member 214 can be rotated in opposite directions about the first and second longitudinal axes 218, 246 until the first and second threaded portions 236, 260 threadably engage. Alternatively, one of the main body 212 and the extension member 214 can be rotated about a corresponding first and second longitudinal axis 218, 246 in a first direction, while the other of the main body 212 and the extension member 214 is not rotated, until the first and second threaded portions 236, 260 threadably engage.

In FIG. 12C, once the first threaded portion 236 threadably engages past the second threaded portion 260 (i.e., once the entire first threaded portion 236 is positioned between the second threaded portion 260 and the bore distal end 258), the main body 212 can rotate freely rotate about the first longitudinal axis 218, and the extension member 214 can rotate freely about the second longitudinal axis 246 without the main body 212 and the extension member 214 threadably disengaging. Moreover, at least a portion of the second connection portion 232 of the main body 212 can move along the second longitudinal axis 246 of the extension member 214 between the second threaded portion 260 and the bore distal end 258. By matingly engaging or snap fitting the slot 240 and the pin 262, the main body 212 and the extension member 214 can be restricted from moving, as shown in FIG. 12D, both axially and rotationally.

Figure 8:
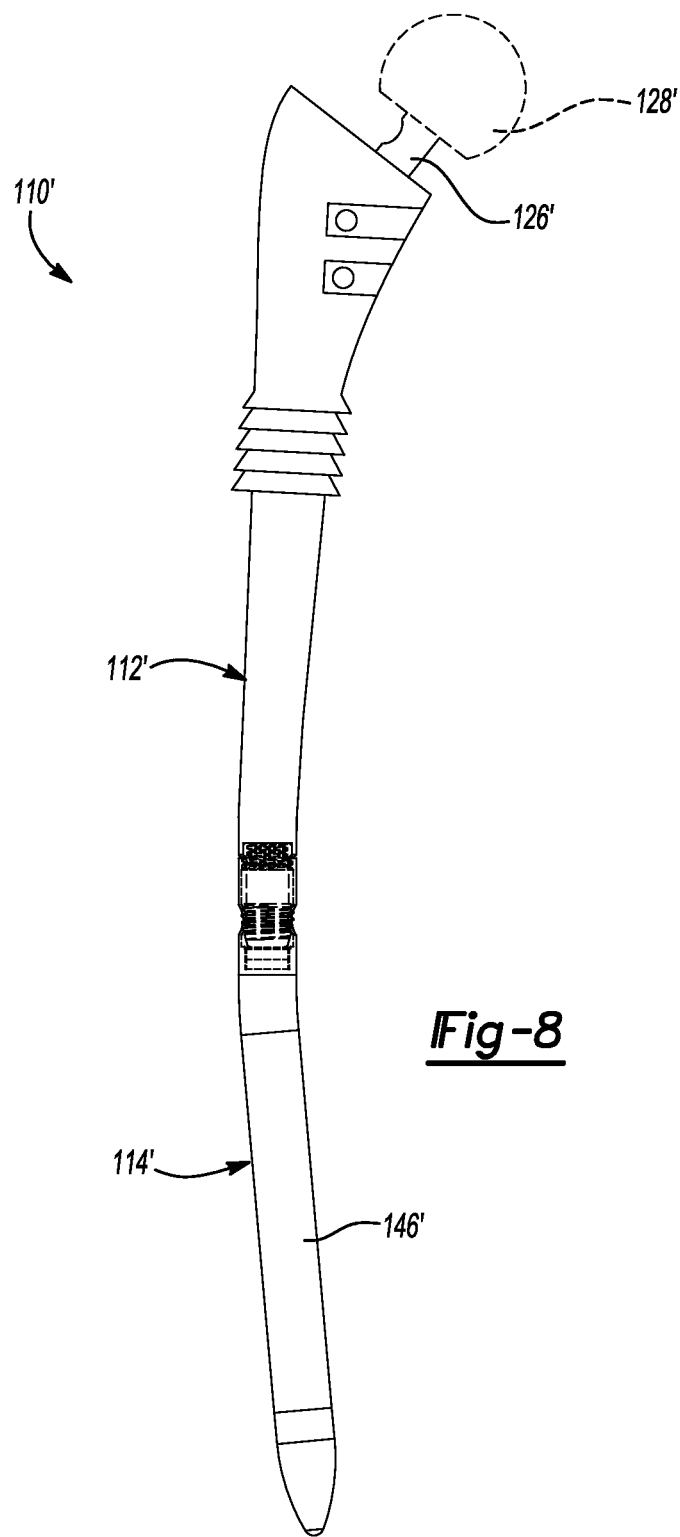
FIG. 8 is an assembled view of a broach system including the main body of FIG. 6A and an extension member according to various embodiments.

The slot 240 and the pin 262 may be formed to provide the extension member 214 at a selected orientation relative to the main body 212 when the two are engaged. For example, the extension member 214 may be curved, as illustrated in FIG. 8, and designed to engage a bone in a selected position relative to the first connection of the assembly. Thus, the mating of the slot 240 and the pin 262 allows the designed configuration to be achieved and maintained.

Disassembly of the main body 212 and the extension member 214 can be accomplished by generally following the above coupling method in reverse. That is, the main body 212 and the extension member 214 can each be pulled apart in opposite directions along the first and second longitudinal axes 218, 246 with a force greater than a force of the mating engagement between the pin 262 and the slot 240. The main body 212 and the extension member 214 can be rotated in opposite directions about the first and second longitudinal axes 218, 246 until the first and second threaded portions 236, 260 threadably disengage. Alternatively, one of the main body 212 and the extension member 214 can be rotated about a corresponding first and second longitudinal axis 218, 246 in a second direction that is different than the first direction, while the other of the main body 212 and the extension member 214 is not rotated, such that the first and second threaded portions 236, 260 threadably disengage.

It is understood that the various embodiments discussed above may be selectively interchanged and are not exclusive. For example, a magnetic portion may be used in combination with the pin and slot 262, 240 coupling. Further, while a threaded engagement was described for initially coupling the main body 12, 112, 212 and the extension member 14, 114, 214, other engagements can be incorporated, such as a non-threaded quarter twist or a bayonet mount, for example. Further, the various extension portions may be provided in a plurality of geometries and lengths and include one or more of the above described coupling mechanisms. Thus, the kit 100 may include a plurality of extension members, each with a different length or geometry, but all including at least one of the coupling mechanisms. The various assemblies may also all be used for similar purposes, such as broaching a bone and/or trialing an implant during a procedure. Other purposes may be preparing other portions for assembly, such as broaching a piping or other solid member.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to broach an anatomy, the system comprising:
a first member including a first length extending between a first end and a second end;
a cutting portion formed along at least a portion of the first length of the first member;
a first connection portion including a second length extending from the second end of the first member to a terminal end, the first connection portion further including a first attachment portion and a second attachment portion, wherein the first attachment portion includes a first threaded portion; and
an extension member that includes a third length extending between a third end of the extension member and a fourth end of the extension member, wherein the extension member includes a third attachment portion and a second threaded portion;
wherein the first threaded portion is configured to engage the second threaded portion in a mating direction;
wherein the first threaded portion is configured to disengage the second threaded portion in the mating direction, such that the first threaded portion is positioned within the extension member beyond the second threaded portion;
wherein the second attachment portion is configured to engage the third attachment portion of the extension member to drive the extension member directly into a bone of the anatomy.

2. The system of claim 1, wherein the extension member further includes a bore extending along a fourth length from the third end to a bore terminal end, the second threaded portion is disposed within the bore near the third end and extends partially along the fourth length towards the bore terminal end.

3. The system of claim 2, wherein:
the extension member further includes a first magnetic portion disposed within the bore, at least a portion of the first member includes a second magnetic portion; and
wherein the first magnetic portion and the second magnetic portion are configured to be magnetically attracted.

4. The system of claim 1, wherein the third attachment portion is configured to matingly engage the second attachment portion of the first member to restrict rotational movement of the first member relative to the extension member once the second threaded portion of the extension member threadably engages past the first threaded portion of the first member.

5. The system of claim 1, wherein the second attachment portion includes a first notch and a first projection, the third attachment portion includes a second notch and a second projection, the first notch is configured to matingly engage the second projection and the second notch is configured to matingly engage the first projection.

6. The system of claim 1, wherein the second attachment portion includes a slot and the third attachment portion includes a pin, wherein the slot is configured to matingly engage the pin.

7. The system of claim 1, wherein an external perimeter of the first member at the second end is substantially equivalent to an external perimeter of the extension member at the third end.

8. The system of claim 1, further comprising:
a second connection portion disposed at the first end of the first member, the second connection portion configured to attach a trial portion or a handle.

9. An assembly to broach an anatomy, the assembly comprising:
an elongated first member extending between a first end and an oppositely located second end, the first member including:
a first member cutting portion; and
a connection portion extending from the oppositely located second end and including a first threaded portion and a first mating feature, wherein in a first arrangement the connection portion is configured to be driven directly into a bone of the anatomy to prepare the bone for an implant; and
an extension member configured to be selectively and removeably coupled with the first member in a second arrangement, the extension member including a second threaded portion and a second mating portion, the second threaded portion is configured to threadably engage the first threaded portion of the first member, the second mating portion is configured to matingly engage the first mating portion of the first member and restrict movement of the first member relative to the extension member once the first threaded portion threadably engages past the second threaded portion, wherein the extension member is configured to be driven directly into the bone of the anatomy to prepare the bone for the implant in the second arrangement.

10. The assembly of claim 9, wherein the extension member has a third end and an oppositely located fourth end, the extension member further has a bore extending from the third end towards the oppositely located fourth end, the second threaded portion is disposed within the bore, the connection portion of the first member is at least partially received in the bore once the second threaded portion of the extension member threadably engages the first threaded portion of the first member and the second mating feature of the extension member matingly engages the first mating feature portion of the first member.

11. The assembly of claim 10, wherein the first mating portion includes a first notch and a first projection, the second mating portion includes a second notch and a second projection, the first notch is configured to matingly engage the second projection and the second notch is configured to matingly engage the second projection.

12. The assembly of claim 11, wherein the extension member further includes a first magnetic portion disposed within the bore, at least a portion the first member includes a second magnetic portion;
wherein the first magnetic portion and the second magnetic portion are configured to be magnetically attracted.

13. The assembly of claim 10, wherein the first mating portion includes a slot and the second mating portion includes a pin, the pin is configured to matingly engage the slot once when the second threaded portion of the extension member threadably engages the first threaded portion of the first member.

14. The assembly of claim 10, wherein the extension member includes a substantially smooth external surface.

15. A method of providing a broach for preparing an anatomy for an implant, the method comprising:
providing a first member including a first end, a second end and a cutting portion formed between the first end and the second end;

providing the first member with first and second connection portions extending from the second end;
configuring the first connection portion to be driven directly into a bone of the anatomy in a first arrangement;
providing an extension member including a third connection portion;
configuring the first connection portion to selectively connect to the third connection portion in a connection direction, such that the first member and the extension member are restricted from moving relative to one another in a second arrangement;
configuring the extension member to be driven directly into a bone of the anatomy in the second arrangement;
configuring the first connection portion to disconnect from the third connection portion in the connection direction in a third arrangement; and
configuring the extension member to be driven directly into a bone of the anatomy in the third arrangement.

16. The method of claim 15 further comprising:
providing the first member with a first notch and a first projection;
providing the extension member with a second notch and a second projection; and
configuring the first notch to matingly engage the second projection and the second notch to matingly engage the second projection to restrict the first member and the extension member from moving relative to one another in the second arrangement.

17. The method of claim 16 further comprising:
providing the extension member with a first magnetic portion;
providing the first member with a second magnetic portion that is magnetically attracted to the first magnetic portion;
configuring the first magnetic portion to magnetically engage the second magnetic portion to further restrict the first member and the extension member from moving relative to one another in the second arrangement.

18. The method of claim 15 further comprising:
providing the first member with a slot;
providing the extension member with a pin; and
configuring the slot to matingly engage the pin to restrict the first member and the extension member from moving relative to one another in the second arrangement.

19. The method of claim 15, further comprising:
providing the extension member with a substantially smooth external surface and a terminal end with a tapered tip; and
configuring the tapered tip to be driven directly into a bone of the anatomy in the second arrangement.

* * * * *

UNITED STATES PATENT AND TRADEMARK OFFICE
CERTIFICATE OF CORRECTION

PATENT NO. : 10,166,031 B2
APPLICATION NO. : 14/500001
DATED : January 1, 2019
INVENTOR(S) : Witt et al.

Page 1 of 1

It is certified that error appears in the above-identified patent and that said Letters Patent is hereby corrected as shown below:

On the Title Page

Item (63), in Column 1, under "Related U.S. Application Data", Line 2, delete "Oct. 19, 2013." and insert --Oct. 29, 2013.-- therefor Signed and Sealed this
Fourteenth Day of April, 2020

Andrei Iancu
*Director of the United States Patent and Trademark Office*